United States Patent
Macfarland et al.

(10) Patent No.: US 9,233,177 B2
(45) Date of Patent: Jan. 12, 2016

(54) METALLOFULLERENE CONTRAST AGENTS

(75) Inventors: Darren K. Macfarland, Danville, VA (US); Robert P. Lenk, Danville, VA (US); Rajesh Shukla, Belle Meades, NJ (US); Kenneth L. Walker, Semora, NC (US); Stephen R. Wilson, Danville, VA (US); Zhiguo Zhou, Winston-salem, NC (US)

(73) Assignee: Luna Innovations Incorporated, Roanoke, VA (US)

( * ) Notice: Subject to any disclaimer, the term of this patent is extended or adjusted under 35 U.S.C. 154(b) by 891 days.

(21) Appl. No.: 12/739,097

(22) PCT Filed: Oct. 22, 2008

(86) PCT No.: PCT/US2008/011996
§ 371 (c)(1),
(2), (4) Date: Feb. 2, 2011

(87) PCT Pub. No.: WO2009/054958
PCT Pub. Date: Apr. 30, 2009

(65) Prior Publication Data
US 2011/0124848 A1    May 26, 2011

Related U.S. Application Data

(60) Provisional application No. 60/960,962, filed on Oct. 22, 2007.

(51) Int. Cl.
| | | |
|---|---|---|
| *A61K 49/00* | (2006.01) | |
| *A61K 49/18* | (2006.01) | |
| *A61K 49/12* | (2006.01) | |
| *B82Y 5/00* | (2011.01) | |
| *C07F 5/00* | (2006.01) | |
| *A61K 47/48* | (2006.01) | |

(52) U.S. Cl.
CPC .............. *A61K 49/189* (2013.01); *A61K 49/12* (2013.01); *B82Y 5/00* (2013.01); *C07F 5/00* (2013.01); *A61K 47/48961* (2013.01)

(58) Field of Classification Search
CPC ............................................. A61K 47/48961
See application file for complete search history.

(56) References Cited

U.S. PATENT DOCUMENTS

| | | | |
|---|---|---|---|
| 5,648,523 | A | 7/1997 | Chiang |
| 6,303,760 | B1 | 10/2001 | Dorn et al. |

(Continued)

FOREIGN PATENT DOCUMENTS

| | | |
|---|---|---|
| JP | H09-87286 A | 3/1997 |
| JP | 2001-114713 A | 4/2001 |

(Continued)

OTHER PUBLICATIONS

Zhang, Bioconjug. Chem., 2010, 21(4), 610-615.*

(Continued)

*Primary Examiner* — Paul Dickinson
(74) *Attorney, Agent, or Firm* — Susan M. Dadio; ATFirm PLLC

(57) ABSTRACT

Endohedral metallofullerene compounds, which in water has a relaxivity of about 30 mM$^{-1}$ S$^{-1}$ to about 300 mM$^{-1}$ S$^{-1}$ and forms a dispersion in water with entities having an average hydrodynamic radius of less than about 20 nm.

9 Claims, 13 Drawing Sheets

Molecular structure of permethylated beta-cyclodextrin

(56) References Cited

U.S. PATENT DOCUMENTS

| | | | |
|---|---|---|---|
| 6,471,942 | B1 | 10/2002 | Miller et al. |
| 2003/0220518 | A1 | 11/2003 | Bolskar et al. |
| 2004/0054151 | A1 | 3/2004 | Dorn et al. |
| 2007/0202413 | A1* | 8/2007 | Wudl et al. ............... 429/304 |

FOREIGN PATENT DOCUMENTS

| | | |
|---|---|---|
| JP | 2003-510340 A | 3/2003 |
| JP | 2005-533745 A | 11/2005 |
| WO | 2005/097808 A2 | 10/2005 |
| WO | WO 2005/097807 A2 | 10/2005 |
| WO | 2007/061036 A1 | 5/2007 |

OTHER PUBLICATIONS

Bolskar, J. Am. Chem. Soc., 2003, 125(18), 5471-5478.*

International Search Report (PCT/ISA/210) issued Jul. 2, 2009 in PCT/US2008/011996.

Written Opinion (PCT/ISA/237) issued Jul. 2, 2009 in PCT/US2008/011996.

T. Grobner, "Gadolinium—A Specific Trigger for the Development of Nephrogenic Fibrosing Dermopath and Nephrogenic Systemic Fibrosis", Nephrology Dialysis Transplantation, 2006, vol. 21, pp. 1104-1108.

P. Fatouros et al., "In Vitro and In Vivo Imaging Studies of a New Endohedral Metallofullerene Nanoparticle", Radiology, 2006, vol. 240, pp. 756-764.

K. Kumar et al., "Macrocyclic Polyaminocarboxylate Complexes of Lanthanides as Magnetic Resonance Imaging Contrast Agents", Pure and Applied Chemistry, 1993, vol. 65, No. 3, pp. 515-520.

M. Botta, "Second Coordination Sphere Water Molecules and Relaxivity of Gadolinium(III) Complexes: Implications for MRI Contrast Agents", Eur. J. Inorg. Chem., 2000, pp. 399-407.

M. Mikawa et al., "Paramagnetic Water-Soluble Metallofullerenes Having the Highest Relaxivity for MRI Contrast Agents," Bioconjugate Chem., 2001, vol. 12, pp. 510-514.

R. Bolskar et al., "First Soluble $M@C_{60}$ Derivatives Provide Enhanced Access to Metallofullerenes and Permit In Vivo Evaluation of $Gd@C_{60}[C(COOH)_2]_{10}$ as a MRI Contrast Agent", J. Am. Chem. Soc., 2003, vol. 125, pp. 5471-5478.

E. Toth et al., Water-Soluble Gadofullerenes: Toward High-Relaxivity, pH Responsive MRI Contrast Agents, J. Am. Chem. Soc. C, 2005, vol. 127, pp. 799-805.

S. Laus et al., "Destroying Gadofullerene Aggregates by Salt Addition in Aqueous Solution of $Gd@C_{60}(OH)_x$ and $Gd@C_{60}[C(COOH)_2]_{10}$", J. Am. Chem. Soc., 2005, vol. 127, pp. 9368-9369.

S. Laus et al., "Understanding Paramagnetic Relaxation Phenomena for Water-Soluble Gadofullerenes", J. Phys. Chem., 2007, vol. 111, pp. 5633-5639.

J. Andre et al., "Synthesis and Physicochemical Characterization of a Novel Precursor for Covalently Bound Macromolecular MRI Contrast Agents", J. Biol. Inorg. Chem., 1999, vol. 4, pp. 341-347.

K. Raymond et al., "Next Generation, High Relaxivity Gd MRI Agents", Bioconjugate Chem., 2005, vol. 16, pp. 3-8.

Darren MacFarland, "Trimetasphere MetallofullereneMRI Contrast Agents with High Molecular Relaxivity", ECS Transactions, Jan. 1, 2008, pp. 117-124,vo. 13, No. 14.

Darren MacFarland et al., "Hydrochalarones: A Novel Endohedral Metallofullerene Platform for Enhancing Magnetic Resonance Imaging Contrast", Journal Of Medicinal Chemistry, Jul. 1, 2008, pp. 3681-83, vol. 51, No. 13.

Chun-Ying Shu et al., "Aggregation Studies of the Water-Soluble Gadofullerene Magnetic Resonance Imaging Contrast Agent: [Gd@C 82 O 6 (OH) 16 (NHCH 2 CH 2 COOH) 8] x", The Journal Of Physical Chemistry B, Aug. 1, 2006, pp. 15597-15601, vol. 110, No. 31.

Chun-Ying Shu et al., "Synthesis and characterization of a new water-soluble endohedral metallofullerene for MRI contrast agents", Carbon, Mar. 1, 2006, pp. 496-500, vol. 44, No. 3.

Balaji Sitharaman et al., "GdGAMMA60[C9COOH2]10 and GdGAMMA60(OH)x: Nanoscale Aggregation Studies of Two Metallofullerene MRI Contrast Agents in Aqueous Solution", Nano Letters, Dec. 8, 2004, pp. 2373-2378, vol. 4, No. 12.

Er-Yun Zhang et al., "Preparation and Characterization of Two Water-Soluble Endohedral Metallofullerence as Magnetic Resonance Imaging Contrast Agents", The Journal of Physical Chemistry B, Dec. 1, 2007, pp. 14223-14226, vol. 111, No. 51.

Australian Patent Examination Report No. 1, issued Feb. 11, 2013 in corresponding application AU 2008317422.

Canadian Requisition by the Examiner, issued Dec. 9, 2014 in corresponding application CA 2703469.

Extended European Search Report including Supplementary European Search Report and European Search Opinion, issued Mar. 9, 2014 in corresponding application EP 08 84 1219.

Japanese Office Action, mailed on Jul. 26, 2013 in corresponding JP 2010-531025 and English language translation thereof.

* cited by examiner

Molecular structure of permethylated beta-cyclodextrin

Proposed structures of PMCD-TMS conjugate (a)  (b)

FIG. 6: Gel electrophoresis of $C_{70}$-monoethyleneglycol amine ($C_{70}$-MEG) (left), Hydrochalarone-1 ($Gd_3N@C_{80}$-MEG) (middle) and Hydrochalarone -3 (right)

FIG. 10
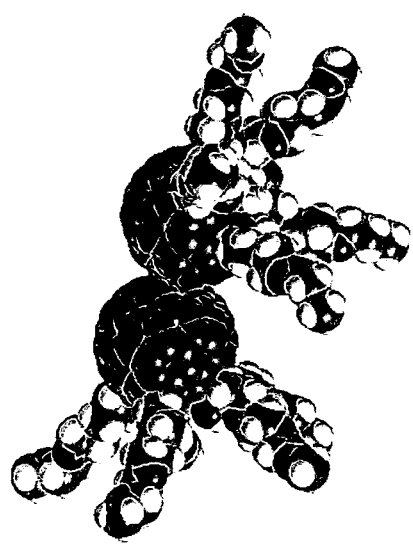 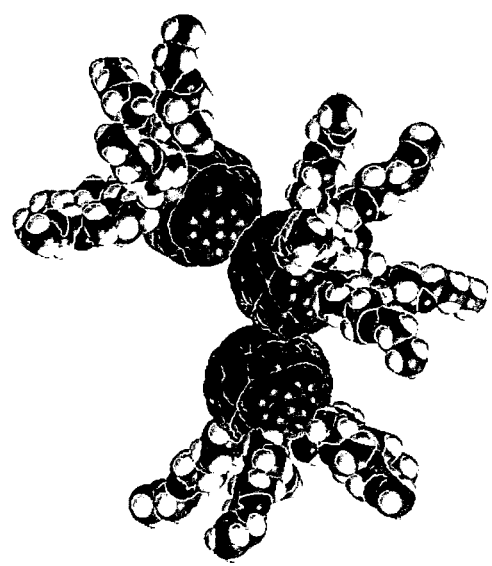
(a) Dimer  (b) Trimer

Elemental analysis for Hydrochalarone-3 with 12 pendant groups ($C_{164}H_{192}O_{48}N_{13}Gd_3$)

|  | C | H | N |
|---|---|---|---|
| Calculated* | 55.34 | 5.34 | 4.39 |
| found | 46.67 | 5.08 | 4.05 |

FIG. 14

METALLOFULLERENE CONTRAST AGENTS

FIELD

This disclosure relates to compounds that are useful in the field of magnetic resonance studies and MRI.

BACKGROUND

Magnetic resonance imaging (MRI) can be used in various medical diagnosis procedures. In general, MRI is based on measuring radio frequency (RF) emissions of water protons in a magnetic field following exposure to an external RF pulse. Parameters used in constructing an image during MRI include the time that it takes for the water protons to relax to their equilibrium state following an RF pulse. The relaxation of water protons following an external RF pulse has two component parameters, designated $T_1$ and $T_2$. Paramagnetic contrast agents affect the $T_1$ component in the relaxivity of water protons, effectively enhancing the contrast during the MRI procedure. On the other hand, ferromagnetic contrast agents affect the $T_2$ component in the relaxivity of water protons. For many applications, agents affecting $T_1$ are preferred because the enhancement provides a brighter image relative to the background.

Elements that have magnetic or paramagnetic properties and cause nearby protons to have a short relaxation time, such as various transition metals, can be used to enhance contrast during MRI procedures. Gadolinium (Gd), with seven unpaired electrons, is particularly effective at enhancing the relaxivity of water during MRI.

SUMMARY

An exemplary embodiment is directed to an endohedral metallofullerene compound, which in water has a relaxivity of about 30 $mM^{-1} \cdot S^{-1}$ to about 300 $mM^{-1} \cdot S^{-1}$ and forms a dispersion in water with entities having an average hydrodynamic radius of less than about 20 nm.

One specific exemplary embodiment is directed to an endohedral metallofullerene compound represented by the formula (I): $A_k X_n N_i @ C_m^*$,
wherein A and X represent identical or different elements in the Periodic Table of Elements, provided that at least one of A and X is paramagnetic, N represents a nitrogen atom;
$C_m^*$ represents a substituted $C_m$;
$C_m$ represents a fullerene comprising m carbon atoms;
k represents an integer from 1 to 3;
n represents an integer from 0 to 2, provided that $1 \leq k+n \leq 3$;
i represents an integer of 0 or 1; and
m represents an even integer from about 60 to about 200,
wherein the substituent(s) in $C_m^*$ comprise one or more groups directly bonded to $C_m$ via at least one atom selected from the group consisting of N, O, S and P.

Another exemplary embodiment is directed to an endohedral metallofullerene compound represented by the formula (II): $A_k X_n N_i @ C_m^{**}$,
wherein $C_m^{**}$ represents a substituted $C_m$; and $C_m$, A, X, N, k, n, i and m have the same meanings as described above;
wherein the substituent(s) in $C_m^{**}$ comprise one or more Z' and optionally one or more Q', wherein Z' comprises a hydrophilic moiety and when there are more than one Z's, Z's are identical or different; and Q' represents a group bonded to $C_m$ via an atom which is selected from the group consisting of N, O, S and P, and when there are more than one Q's, Q's are identical or different.

Yet another exemplary embodiment is directed to an endohedral metallofullerene compound represented by the formula (III): $A_k X_n N_i @ C_m'$,
wherein $C_m'$ represents an optionally substituted fullerene having one or more missing carbon atoms and/or bonds derived from $C_m$, and $C_m$, A, X, N, k, n, i and m have the same meanings as described above.

As described herein, the endohedral metallofullerene compounds represented by the formulae (I), (II) and (III) can have relatively high stability and relaxivity that is intrinsic to the fullerene derivatives themselves and not due to large aggregation. These endohedral metallofullerene compounds can be useful as MRI contrast agents, in particular, contrast agents that are targeted to specific sites.

BRIEF DESCRIPTION OF THE DRAWINGS

FIGS. 10(a) and (b) illustrate exemplary endohedral metallofullurene dimer and trimer, respectively.

FIG. 14 shows the elemental analysis of Hydrochalarone-3.

DETAILED DESCRIPTION OF EMBODIMENTS

Figure 1:
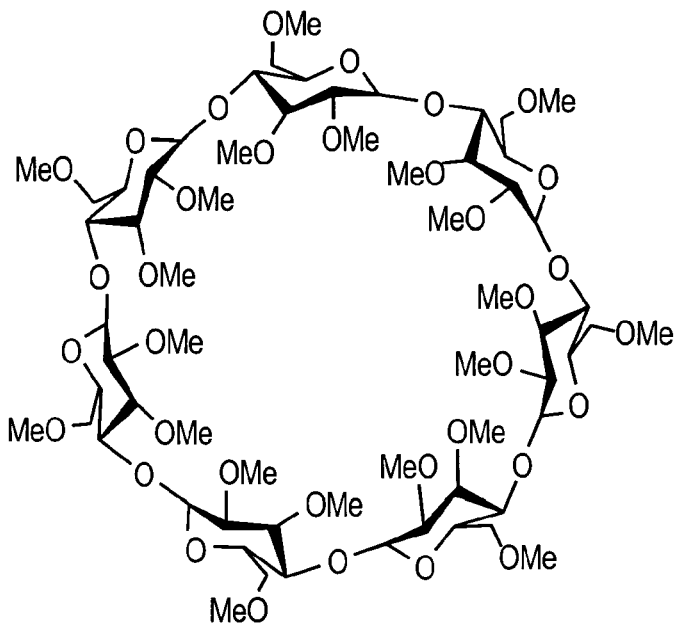
FIG. 1 shows a molecular structure of permethylated beta-cyclodextrin.

Among the many qualities that impact the usefulness of contrast agents is relaxivity. The mechanism by which Gd-based contrast agents affect the relaxivity of water protons has been a subject of investigation. The degree of relaxivity enhancement by Gd is a function of Gd's proximity to water protons and dynamics of water in the vicinity of the Gd. For conventional compounds, the influence of Gd on enhancing the relaxivity of water protons is described by the Solomon- Bloembergen-Morgan equation. Components that primarily contribute to relaxivity of a contrast agent are: the number of water coordination sites, q, the time the water stays bound to this site, $\tau_m$, and the rotational rate, $\tau_r$. These parameters relate to the interaction of Gd in a contrast agent with an inner sphere of water molecules. There can also be interactions between Gd and water molecules through an outer sphere of water molecules in a hydration shell. However, the contribution of the outer sphere interactions is difficult to measure because the inner sphere component dominates. See, e.g., M. Botta, *Second Coordination Sphere Water Molecules and Relaxivity of Gadolinium(III) Complexes: Implications for MRI Contrast Agents*, Eur. J. Inorg. Chem., pages 399-407 (2000).

Since Gd and many of the other known relaxivity enhancing elements are toxic, they can only be used when trapped in some structure that sequesters them from sites where they can cause deleterious effects. Current technology for formulating Gd-based contrast agents relies on chelates where Gd is bound by charged groups within the chelate via ionic bonds or electrostatic interactions. A number of such products that are currently on the market employ various linear and macrocyclic chelates. However, the binding of gadolinium to chelates is not permanent. Gadolinium can disassociate from the chelates before being eliminated from a patient. Recent evidence suggests that, when used in some patients, especially those with impaired glomerular filtration rates, Gd chelates may cause a potentially fatal disease called nephrogenic systemic fibrosis (NSF) ("gadolinium poisoning"). See, Grobner, T., *Gadolinium—A Specific Trigger for the Development of Nephrogenic Fibrosing Dermopath and Nephrogenic Systemic Fibrosis*, Nephrol. Dial Transplant, Vol. 21, pages 1104-08 (2006).

In addition, the currently available contrast agents have relatively low relaxivities, ranging between about 4 to 8 $mM^{-1} \cdot S^{-1}$. When a contrast agent having low relaxivity is utilized, it is necessary to introduce a higher concentration of the contrast agent to achieve a desired level of contrast. Generally, agents with relaxivities above 20 $mM^{-1} \cdot S^{-1}$ would be preferred because a relatively smaller amount of Gd is needed to achieve an acceptable level of contrast.

Higher relaxivity agents are especially preferred for contrast agents designed to accumulate at a particular target to reveal specific anatomical details about that target. When a contrast agent having a relatively high relaxivity is used, a lower concentration of the agent will produce sufficient signal detectable above the background noise.

Endohedral fullerenes containing Gd (one type of "metallofullerenes") have also been studied as an alternative technology for introducing Gd as a contrast agent, where Gd atoms are encapsulated within the fullerene. See, for example, WO 2005/097807. Endohedral metallofullerenes are presumed to be safer because the carbon cages of fullerenes are held together by covalent bonds which are unbreakable under physiological conditions, and as such, the encapsulated Gd atom(s) can be prevented from departing the fullerene cages and interacting with tissues.

Fullerenes are a third allotrope of carbon and are insoluble in water. Therefore, to effectively use endohedral metallofullerenes as biological tools, it is necessary to modify their surface, e.g., by addition of groups that render the fullerenes soluble. See, e.g., U.S. Pat. No. 5,648,523.

Several investigators have reported that endohedral metallofullerenes containing Gd or other atoms can be made water soluble by attaching multiple hydroxyl groups to the carbon atoms on the fullerene cage. See, e.g., U.S. Pat. No. 6,471,942; U.S. Patent Application Publication No. 2004/0054151; Mikawa et al., *Paramagnetic Water-Soluble Metallofullerenes Having the Highest Relaxivity for MRI Contrast Agents*, Bioconjug. Chem., Vol. 12, pages 510-4 (2001); and Fatouros et al., *In Vitro and In Vivo Imaging Studies of a New Endohedral Metallofullerene Nanoparticles*, Radiology, Vol. 240, pages 756-764 (2006).

It was originally believed that metallofullerenes would have poor relaxivities because the enclosure of metals, such as Gd, within the cage limits the proximity to which water molecules can approach the Gd atom(s). Therefore, there is no inner sphere component to the transfer mechanism of the paramagnetic Gd to water protons. The influence of the magnetic field on the Gd atom is believed to drop off proportional to $R^{-6}$ (R is the distance between the Gd atom and the water molecule). See, e.g., Kumar et al., *Macrocyclic Polyaminocarboxylate Complexes of Lanthanides as Magnetic Resonance Imaging Contrast Agents*, Pure and Applied Chemistry, Vol. 65, pages 515-520 (1993).

Surprising, relatively high relaxivities were observed with polyhydroxylated metallofullerenes. See, e.g., Bolskar et al., *First Soluble $M@C_{60}$ Derivatives Provide Enhanced Access to Metallofullerenes and Permit In Vivo Evaluation of $Gd@C_{60}[C(COOH)_2]_{10}$ as a MRI Contrast Agent*, J. Am. Chem. Soc., Vol. 125, pages 5471-78 (2003); Mikawa et al., *Paramagnetic Water-Soluble Metallofullerenes Having the Highest Relaxivity for MRI Contrast Agents*, Bioconjug. Chem., Vol. 12, pages 510-4 (2001); Toth et al., *Water-Soluble Gadofullerenes: Toward High-Relaxivity, pH Responsive MRI Contrast Agents*, J. Am. Chem. Soc., Vol. 127, pages 799-805 (2005); Fatouros et al., *In Vitro and In Vivo Imaging Studies of a New Endohedral Metallofullerene Nanoparticles*, Radiology, Vol. 240, pages 756-764 (2006); and WO 2005/097807.

However, recent in-depth study of the contrast behavior of $Gd@C_{60}(OH)_n$ using $^{17}O$ relaxivity measurements has shown that the high relaxivity of polyhydroxylated gadofullerenes observed in water is substantially altered when solutes are present which disaggregate the $Gd@C_{60}(OH)_n$. See, e.g., Laus et al., *Destroying Gadofullerene Aggregates by Salt Addition in Aqueous Solution of $Gd@C_{60}(OH)_x$ and $Gd@C_{60}[C(COOH)_2]_{10}$*, J. Am. Chem. Soc., Vol. 127, pages 9368-69 (2005); and Laus et al., *Understanding Paramagnetic Relaxation Phenomena for Water-Soluble Gadofullerenes*, J. Phys. Chem., Vol. 111, page 5633-39 (2007).

In other words, the relatively high relaxivity of polyhydroxylated gadofullerenes is due to the presence of large aggregates of polyhydroxylated gadofullerenes. When the aggregates are eliminated, e.g., upon treatment with a phosphate buffered saline (PBS) buffer solution or addition to biological fluids, such as human serum, the relaxivity of polyhydroxylated gadofullerenes becomes negligible. See, e.g., Laus et al., *Destroying Gadofullerene Aggregates by Salt Addition in Aqueous Solution of $Gd@C_{60}(OH)_x$ and $Gd@C_{60}[C(COOH_2)]_{10}$*, J. Am. Chem. Soc., Vol. 12, pages 9368-69 (2005); and Laus et al., *Understanding Paramagnetic Phenomena for Water-Soluble Gadofullerenes*, J. Phys. Chem., Vol. 111, pages 5633-39 (2007). For at least this reason, these polyhydroxylated gadofullerenes are undesirable as MRI contrast agents in biological applications.

The term "endohedral metallofullerene compound," as used herein, encompasses a compound having one endohedral metallofullerene in its molecule and aggregates thereof, and a compound having two or more endohedral metallofullerene monomeric units covalently bonded to each other and aggregates thereof. In particular, the compound having two or more endohedral metallofullerene monomeric units covalently bonded to each other may include dimer, trimer, oligomer, polymer, etc. The bonding manner of the monomeric units are not particularly limited. For example, a dimer of two monomers represented by formula A-B may be represented by formula A-B-A-B (head-to-tail), A-B-B-A (tail-to-tail), B-A-A-B (head-to-head),

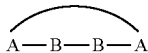

(head-to-head and tail-to-tail), etc. In addition, these compounds may be present individually or in combination thereof. The endohedral metallofullerene compounds may be charged and consequently there may be counter balancing ions. In one embodiment, the endohedral metallofullerene compound may have one or more negative charges. The counter cation may be any positively charged species present in the medium. Specific examples of the cations may include, but are not limited to, $H^+$, protonated amine reagent used in the reaction, e.g., protonated MEG, and protonated Trizma, if Trizma (i.e., tris(hydroxymethyl)amino methane) is used following the reaction.

The term "endohedral metallofullerene," as used herein, denotes a fullerene where one or more metal atoms are encapsulated inside a fullerene cage network. Accepted symbols for elements and subscripts to denote numbers of elements are used herein. Generally, all elements to the right of an @ symbol are part of the fullerene cage network, while all elements listed to the left of the @ symbol are contained within the fullerene cage. For example, under the notation $Sc_3N@C_{80}$, the $Sc_3N$ trimetallic nitride is situated within a $C_{80}$ fullerene cage.

The term "TRIMETASPHERE®" (TMS), as used herein, denotes a member of a family of endohedral metallofullerenes which contain a trimetallic nitride compound in the fullerene cage. For example, GdTMS refers to a Gd containing TRIMETASPHERE®. Suitable TRIMETASPHERE®s include those discussed in U.S. Pat. Nos. 6,303,760 and 6,471,942, and U.S. Patent Application Publication No. 2004/0054151.

The term "relaxivity," as used herein, is a measure of the efficacy of paramagnetic complexes in shortening the time for relaxation processes and hence increasing the relaxation rate, at 1 mM (millimole) concentration of the metallofullerene molecules. A large relaxivity value usually reflects a better in vivo performance of a paramagnetic complex as a contrast agent.

The term "dispersion," as used herein, denotes a heterogeneous mixture containing two separate phases: a dispersed phase and a continuous phase. As described herein, the dispersed phase is made of particles or aggregates of endohedral metallofullerenes that are distributed throughout the continuous phase.

The term "hydrodynamic radius," as used herein, denotes the radius of a sphere having equivalent hydrodynamic properties as a given structure.

The term "aggregate," as used herein, denotes collection of units or particles forming a body or mass.

Endohedral Metallofullerene Compounds

The present disclosure describes endohedral metallofullerene compounds, which in water has a relaxivity of about 30 $mM^{-1} \cdot S^{-1}$ to about 300 $mM^{-1} \cdot S^{-1}$ and forms a dispersion in water with entities having an average hydrodynamic radius of less than about 20 nm.

In one embodiment, the endohedral metallofullerene compound has one or more negative charges.

In an embodiment, an endohedral metallofullerene compound is represented by the formula (I): $A_k X_n N_i @ C_m^*$.

In the formula (I), A and X represent identical or different elements in the periodic table of elements, provided that at least one of A and X is paramagnetic. In one embodiment, at least one of A and X represents an element having one or more unpaired electrons. In a preferred embodiment, at least one of A and X represents a rare earth element, a group IIIB element in the periodic table of elements or the like. Examples of suitable rare earth elements and group IIIB elements may include, but are not limited to, scandium (Sc), erbium (Er), holmium (Ho), yttrium (Y), lanthanum (La), gadolinium (Gd), thulium (Tm), dysprosium (Dy), terbium (Tb) and ytterbium (Yb). N represents a nitrogen atom.

In addition, k represents an integer from 1 to 3, n represents an integer from 0 to 2, and i represents 0 or 1. Preferably, k+n is 1, 2 or 3.

$C_m^*$ represents a fullerene $C_m$ that is substituted by one or more substituents where m represents an integer, in particular, an even value, from about 60 to about 200. In one embodiment, m is 60, 68, 70, 74, 78, 80, 82, 90, 92, 94 and the like. Further, when i is 0, m is preferably an integer from about 60 to about 82.

In one embodiment, the substituents in $C_m^*$ can include one or more groups, which are directly bonded to $C_m$ via an atom having relatively high electronegativity. Preferably, the atom having relatively high electronegativity is selected from the group consisting of N, O, S and P. However, the compounds represented by the formula (I) do not include $Gd@C_m^*$, wherein the substituent(s) in $C_m^*$ consist of at least one of OH or C(COOH)$_2$, and in particular, $Gd@C_{60}(OH)_n$, $Gd@C_{60}[C(COOH)_2]_n$, $Gd@C_{82}(OH)_n$ and $Gd@C_{82}[C(COOH)_2]_n$ mentioned above.

In a further embodiment, the substituent(s) in $C_m^*$ is represented by -Q-$Z_j G_p D_r$. Q represents an atom selected from the group consisting of N, O, S and P. Z, G and D are different, and each comprises a hydrophilic moiety. In addition, Z, G and D each is bonded to $C_m$ through Q. Further, j represents an integer from 1 to 3; p represents an integer from 0 to 2; and r represents an integer from 0 to 2. Preferably, 1≤p+j+r≤3. The phrases "bonded to" and "attached to," as used herein, denote covalent bonding, via either a single bond or a multiple bond, such as a double bond and a triple bond. When a double or triple bond is present, it can be formed between one, two or three atoms, at one end, adjacent or not, and one, two or three atoms, at the other end, adjacent or not.

In one embodiment, the hydrophilic moiety in Z, G and/or D can preferably contain one or more oxygen atoms.

Examples of suitable substituents in $C_m^*$ may include, but are not limited to, >O (epoxide), a polyethylene glycol moiety, a sugar group, a zwitterionic group, an amino acid group and derivatives thereof. Short peptides, such as groups containing more than one amino acid subunit, may also be used as substituents in $C_m^*$.

As the polyethylene glycol moiety, a polyethylene glycol group represented by formula $CH_3(OCH_2CH_2)_h$—, wherein h is 1 or more, may be preferably used. More preferably, h represents an integer from 1 to 20.

Examples of suitable sugar groups may include, but are not limited to, permethylated cyclodextrins (PMCDs). PMCDs, as exemplified below, are readily available highly water solubilizing compounds that can provide suitable sites for binding water molecules in proximity to the endohedral metallofullerene, as exemplified in FIG. 1.

Figure 2:
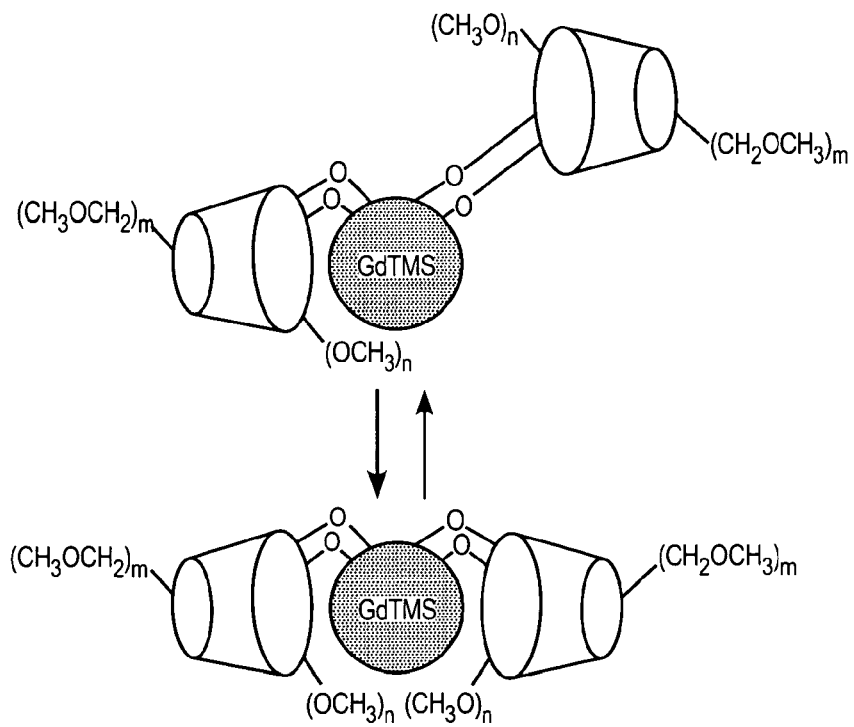
FIG. 2 illustrates proposed structures of PMCD-TMS conjugate.

When PMCD is covalently bonded to the fullerene ring of an endohedral metallofullerene, such as a GdTMS, at least one bond is formed between an oxygen atom in the PMCD molecule and TMS. A possible structure of a PMCD-GdTMS conjugate is shown in FIG. 2, where m could be 6, 7 or 8 for alpha-, beta- or gamma-cyclodextrins, respectively.

At least one and perhaps two PMCD are bonded onto each fullerene cage. In addition, the CD groups in the PMCD molecule can interact with the GdTMS unit, to thereby partially encapsulate the sphere surrounding the GdTMS unit.

PMCD can provide sufficient wetting of the fullerene surface and therefore improve the water solubility thereof. The magnetic moment of paramagnetic metals inside the fullerene cage can be transferred to the bulk water, thus providing contrast effects. However, cyclodextrins without the methyl groups tend to form large aggregates, and are not preferred.

Examples of suitable zwitterionic groups may include, but are not limited to, a phosphocholine group.

Examples of suitable amino acid groups may include, but are not limited to, alanine, asparagine, cysteine, glutamine, glycine, isoleucine, leucine, methionine, phenylalanine, proline, serine, theonine, tryptophan, tyrosine, valine, asparagine, aspartic acid, glutamine, glutamic acid, arginine, histidine, lysine and combinations thereof.

In another embodiment, the substituent in $C_m^*$ can contain one or more hydrophilic moieties bonded to $C_m$ via an oxygen linkage, a nitrogen linkage, a N-hydroxyamino linkage, a sulfur linkage, a sulfate linkage, a phosphate linkage or a phosphoester linkage.

Also described herein are endohedral metallofullerene compounds represented by the formula (II): $A_k X_n N_i @ C_m^{**}$.

In the formula (II), $C_m$, A, X, N, k, n, i and m have the same meanings as described herein with respect to the formula (I).

$C_m^{}$ represents a $C_m$ that is substituted by one or more substituents. The substituents in $C_m^{}$ can contain one or more Z' and optionally one or more Q'. Z' represents a hydrophilic moiety-containing group. When there are more than one Z's in $C_m^{}$, Z's can be identical or different. Q' represents a group bonded to $C_m$ via a relatively electronegative atom, and preferably, an atom of N, O, S, P and the like. Moreover, when there are more than one Q's in $C_m^{}$, Q's can be identical or different.

In one embodiment, the hydrophilic moiety for Z' can preferably contain one or more oxygen atoms.

Examples of suitable Z' substituents in $C_m^{**}$ may include, but are not limited to, a polyethylene glycol moiety, a sugar group, a zwitterionic group, an amino acid group and derivatives thereof, and a short peptide, as described herein with respect to the formula (I).

In another embodiment, the Q' substituent in $C_m^{**}$ can represent a group bonded to $C_m$ via an oxygen linkage, a nitrogen linkage, a N-hydroxyamino linkage, a sulfur linkage, a sulfate linkage, a phosphate linkage or a phosphoester linkage.

Further described herein are endohedral metallofullerene compounds represented by the formula (III): $A_k X_n N_i @ C_m'$.

In the formula (III), $C_m'$ represents an optionally substituted fullerene having one or more missing carbon atoms and/or bonds derived from $C_m$, and thus has one or more "holes" on the fullerene cage. Preferably, the holes on the fullerene cage have a dimension which can allow passage of water molecules and not the metal component encapsulated inside the cage network. $C_m$, A, X, N, k, n, i and m have the same meanings as described herein with respect to the formula (I).

Generally, $C_m'$ has an approximately spherical skeleton consisting predominantly of 5- and 6-membered carbon rings. The substitutent(s) on $C_m'$, if present, can be selected from the substituents described above for $C_m^*$ in the formula (I), and Z' and Q' described above for $C_m^{**}$ in the formula (II).

Figure 3:
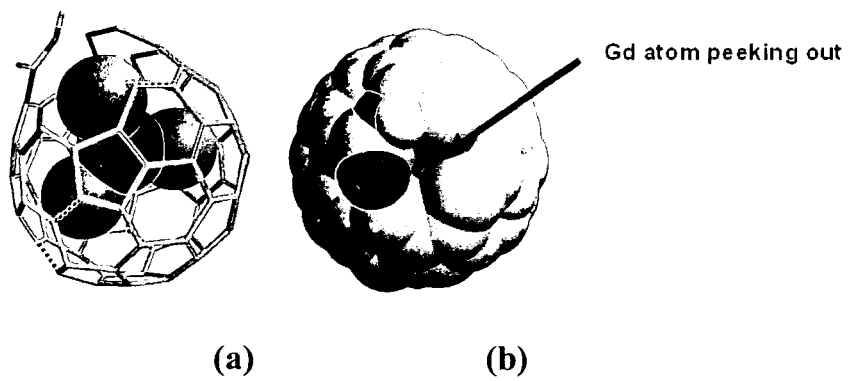
FIG. 3(a) illustrates a stick model of one example of $C_m'$ and FIG. 3(b) is a space-filling model thereof showing a small hole.

In one embodiment, $C_m'$ is substituted by one or more >O and/or —COOH. FIG. 3(a) illustrates a stick model of one example of $C_m'$ and FIG. 3(b) is a space-filling model thereof showing a small hole.

In a further embodiment, $A_k X_n N_i @ C_m^*$, $A_k X_n N_i @ C_m^{**}$ and $A_k X_n N_i @ C_m'$ may represent $Gd@C_{60}^*$, $Gd@C_{82}^*$ or $Gd_3N@C_{80}^*$, $Gd@C_{60}^{}$, $Gd@C_{82}^{}$ or $Gd_3N@C_{80}^{**}$, and $Gd@C_{60}'$, $Gd@C_{82}'$ or $Gd_3N@C_{80}'$, respectively.

As described herein, the substituents in $C_m^*$ of the formula (I), $C_m^{**}$ of the formula (II), and $C_m'$ of the formula (III) may further contain one or more halogen atoms, such as chlorine, directly covalently bonded to the fullerene cage.

The endohedral metallofullerene compounds represented by the formulae (I), (II) and (III) preferably have a relaxivity in water of greater than about 30 mM$^{-1}$·S$^{-1}$ to about 300 mM$^{-1}$·S$^{-1}$, more preferably, greater than 40 mM$^{-1}$·S$^{-1}$, and most preferably, greater than 60 mM$^{-1}$·S$^{-1}$. The term "about," as used herein, may denote a deviation of ±30%, and preferably, ±20%, ±10%, ±5%, ±2% or ±1%. The term "water," as used herein, denotes water substantially free of any additional components. In one embodiment, deionized (DI) water can be used.

Relaxivity of endohedral metallofullerene compounds strongly depends on the size of the aggregate particles thereof. An average hydrodynamic radius or diameter of particles reflects the aggregation degree of the particles in a medium. For example, Lon Wilson in *First Soluble M@C$_{60}$ Derivatives Provide Enhanced Access to Metallofullerenes and Permit in Vivo Evaluation of Gd@C$_{60}$[C(COOH)$_2$]$_{10}$ as a MRI Contrast Agent*, J. Am. Chem. Soc., Vol. 125, 5471-78 (2003), reported that a poly(OH) modified Gd@C$_{60}$ has a relaxivity of 80 mM$^{-1}$·S$^{-1}$ when the hydrodynamic diameter ($D_H$) thereof is about 600 nm. However, the relaxivity drops to less than 10 mM$^{-1}$·S$^{-1}$ when the $D_H$ gets down to 100 nm. An individual endohedral metallofullerene molecule is believed to have a diameter of about 2 nm to about 3 nm.

Dynamic light scattering studies showed that the high relaxivity of these gadofullerenes was due to aggregates that were hundreds of nm in size. However, the aggregates dissociate rapidly in biological fluids and the high relaxivity is lost.

Without wishing to be bound by theory, one possible explanation for the high relaxivity of metallofullerene aggregates is that water molecules are confined in the interstices of the aggregates, and that aggregates have a slower tumbling rate, which affects the coupling mechanism between the paramagnetic metal, such as Gd, and water protons, in particular, rotational correlation time, $\tau_r$.

It was believed that slower rotational time is a key to improving relaxivity. See, e.g., Maecke et al., *Synthesis and Physicochemical Characterization of a Novel Precursor for Covalently Bound Macromolecular MRI Contrast Agents*, J. Biol. Inorg. Chem., Vol. 4, pages 341-7 (1999). However, the results from subsequent studies of various formulation experiments that showed relaxivities were found to be inconsistent with the hypothesis that the key to obtaining high relaxivity is the rotational correlation time of Gd. See, e.g., Raymond et al., *Next Generation, High Relaxivity Gd MRI Agents*, Bioconjugate Chem. Vol. 16, pages 3-8 (2005).

Figure 4:
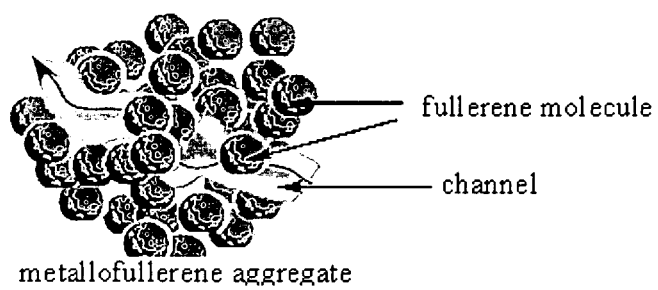
FIG. 4 illustrates a theory that may explain the relaxivity enhancing effects of aggregated Gd metallofullerene.

Although not wishing to be bound by any theory, it is believed that the high relaxivity observed in endohedral metallofullerene aggregates may be due to a slower water diffusion rate through the aggregates. Specifically, as depicted in the cartoon illustration of FIG. 4, the aggregates are actually porous clusters, and have channels through them which can hinder the diffusion of water molecules significantly, compared to the free water molecules.

As a result of slower diffusion of water molecules, the water protons would have a longer period of time to be in close proximity to the metal, such as Gd, in the metallofullerene cage, resulting in higher relaxivity.

As described herein, endohedral metallofullerenes can be modified with one or more hydrophilic moiety-containing substituents, by bonding to the metallofullerenes directly or via a relatively electronegative atom, such as N, O, S and P.

Figure 5:
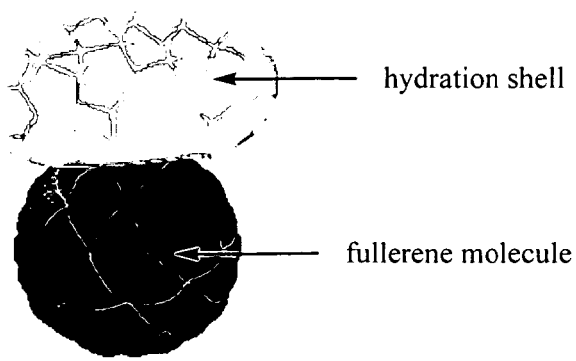
FIG. 5 illustrates one possible theory explaining the relaxivity enhancing effects of molecules represented by formula (I) or (II).

Without wishing to be bound by any theory, it is believed that there are four components to the interaction of the endohedral metallofullerene compounds represented by the formulae (I), (II) and (III) (with substituent(s)) with water molecules. First, the electronegative atoms, which are directly bonded to the fullerene cage and/or neighboring atoms, can interact with water molecules, e.g., via hydrogen bonding or other electrostatic interactions, thereby bringing the water molecules close to the fullerene cage as well as the metal atom(s) encapsulated therein. Second, as depicted in the cartoon illustration of FIG. 5, a hydration shell can be formed by the hydrophilic moieties attached to the fullerene cage $C_m$, through which the water molecules have to diffuse to reach the attachment points on the fullerene cage. Third, the branches on the fullerene cage can provide additional steric hindrance, thereby further impeding diffusion of the water molecules in the vicinity of the fullerene cage. Fourth, when a fullerene cage has one or more holes, e.g., in the formula (III), the exposed gadolinium can directly interact with water molecules (FIG. 3(*b*)).

With respect to the formula (III), it is also possible that water molecules pass through the holes on the fullerene cage and enter inside the cage. These water molecules are at least temporarily entrapped inside the fullerene cage until they find their way out of the cage through the holes. Further, the water molecules inside the fullerene cage may further interact, or even become coordinated, with the metal therein. In such case, the entrapped water molecules may be prevented from diffusing away from the fullerene cage.

By confining water molecules in the hydration shell and/or hindering diffusion of water molecules, or inside the fullerene cage, it is possible to effect interaction between the water molecules and paramagnetic metal atom(s) within the fullerene cage for a longer period of time, thereby optimizing $\tau_m$. Therefore, the endohedral metallofullerene compounds described herein can exhibit relatively high intrinsic relaxivity, not merely resulting from large aggregates.

Metallofullerenes having many hydroxyl groups directly bonded to the fullerene cage tend to form relatively large aggregates. Thus, in a preferred embodiment, the substituents in $C_m$* of the formula (I), $C_m$** of the formula (II), and $C_m'$ of the formula (III) do not contain many hydroxyl groups directly covalently bonded to the fullerene cage.

The endohedral metallofullerene compounds of the formulae (I), (II) and (III) preferably form a dispersion in water with entities having an average hydrodynamic radius of less than about 20 nm. Unlike aggregates, these compounds do not "disassociate" in biological fluids.

The endohedral metallofullerene compounds of formulae (I), (II) and (III) have relatively high relaxivities and can provide improved image quality, including visualization of the vasculature system, in MRI procedures.

In addition, these endohedral metallofullerene compounds can have excellent chemical stability. Generally, the fullerene cage will not break apart at a temperature of less than about 250° C. in air or unless being exposed to concentrated hot nitric acid, such as 70% nitric acid at 95° C.

Moreover, when the endohedral metallofullerenes are used in MRI procedures, the encapsulated metal, such as gadolinium, is stably enclosed in a closed carbon cage and thus is prevented from entering and interacting with tissues of a subject so as to cause undesired effects. (The holes in $C_m'$ (Formula (III)) are not large enough for Gd to escape.) Thus, these endohedral metallofullerene compounds can be used in all patients, including those with impaired renal function.

In addition, the rigid fullerene cage in the compounds can allow the attachment of adducts having desired functionality or properties, e.g., those which can achieve a hydration shell surrounding the endohedral metallofullerene, without degrading the stability thereof.

Furthermore, due to their relatively high stability and enhanced relaxivities in biological environment, the endohedral metallofullerene compounds described herein may also be used in targeted imaging. For example, the rigidity of the fullerene cage and large number of potential attachment sites on the fullerene cage permit attachment of targeting moieties in addition to groups capable of increasing $\tau_m$. These endohedral metallofullerene compounds may act as a module to construct MRI contrast agent that are targeted to specific sites. For example, one or more targeting species may be additionally attached to the fullerene cage of endohedral metallofullerene compounds, such as those represented by the formulae (I), (II) and (III). Examples of suitable targeting moieties may include, but are not limited to, cholesterol, L-3,4-dihydroxyphenylalanine (L-DOPA), tropane or its derivatives, tetrabenazine, urushiol, transferrin, muc-1, antibodies (polyclonal or monoclonal), cytokines, saccharides (such as glucose, mannose and ribose) or polysaccharides, glutamate and aminolevulinic acid.

These targeted agents comprising an endohedral metallofullerene contrast agent with one or more targeting moieties preferably selectively accumulate at specific sites to provide detailed anatomical information about those sites. This approach may provide a substantial improvement in diagnosis and management of certain diseases.

In preferred embodiments, the hydration shell of the endohedral metallofullerene contrast agents described herein can enhance the solubility of the endohedral metallofullerene compounds and help preventing the formation of large aggregates, which can have severe toxicity issues.

The endohedral metallofullerene contrast agents described herein may have a relatively high solubility in water and/or other organic solvents, such as ether. For instance, the solubility of $Gd_3N@C_{80}/NH_2CH_2CH_2OCH_3$ adduct ("Hydrochalarone-1") in water is about 100 mg/mL. This figure is roughly two orders of magnitude above the highest values for the known fullerenes and their derivatives. In an embodiment, the fullerene derivative described herein has a water solubility of greater than about 40 mg/mL. Further, the solubility of $Gd_3N@C_{80}/NH_2(CH_2)_{11}CH_3$ adduct in ether is greater than about 10 mg/mL.

The improved water solubility allows the endohedral metallofullerene derivatives described herein to be more compatible with biological systems and thus makes them potentially useful as MRI contrast agents.

The increased solubility is believed to be attributable to the attachments on the fullerene cage. In addition, a charge residing on the cage may also be accountable for the increased water solubility. For example, gel electrophoresis experiments show that $Gd_3N@C_{80}/NH_2(CH_2CH_2O)_3CH_3$ adduct ("Hydrochalarone-3") bears a negative charge (FIG. 6).

Figure 6:
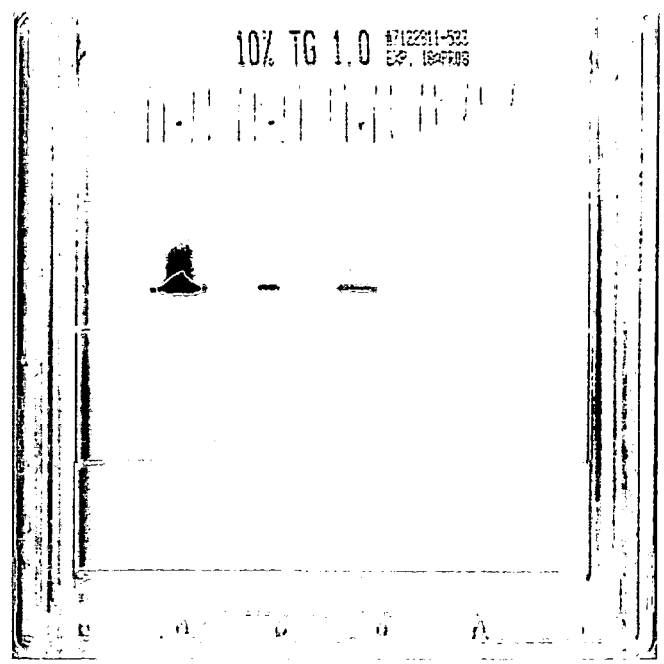
FIG. 6 is a photograph of the gel electrophoresis data of $C_{70}$-monoethyleneglycol amine ($C_{70}$-MEG), Hydrochalarone-1 ($Gd_3N@C_{80}$-MEG) and Hydrochalarone-3.

Specifically, FIG. 6 shows gel electrophoresis results of $C_{70}$-monoethyleneglycol amine ($C_{70}$-MEG) (left), Hydrochalarone-1 ($Gd_3N@C_{80}$-MEG) (middle) and Hydrochalarone-3 (right) moving toward cathode (bottom). The gel electrophoresis was conducted according to Novex® Tris- Glycine polyacrylamide gel chemistry (Novex® 10% Tris-Glycine Gel 1.0 mm, 10 well). Novex® Tris-Glycine polyacrylamide gel chemistry is based on the Laemmli system (1) with minor modifications for maximum performance in the pre-cast format. These gels do not contain SDS and can therefore be used to accurately separate both native and denatured proteins. Novex® Tris-Glycine Gels are made with high-purity, strictly quality-controlled reagents: Tris base, HCl, acrylamide, bisacrylamide, TEMED, APS, and highly purified water. They do not contain SDS. Tris-Glycine Running Buffer without SDS is used as buffer. The testing sample is prepared by combining 25 uL of each sample with 5 uL of glycerol per well. The current is loaded @ 50 Volts (20 minutes) and then increased to 120 Volts (30 minutes) once loaded.

Figure 7:
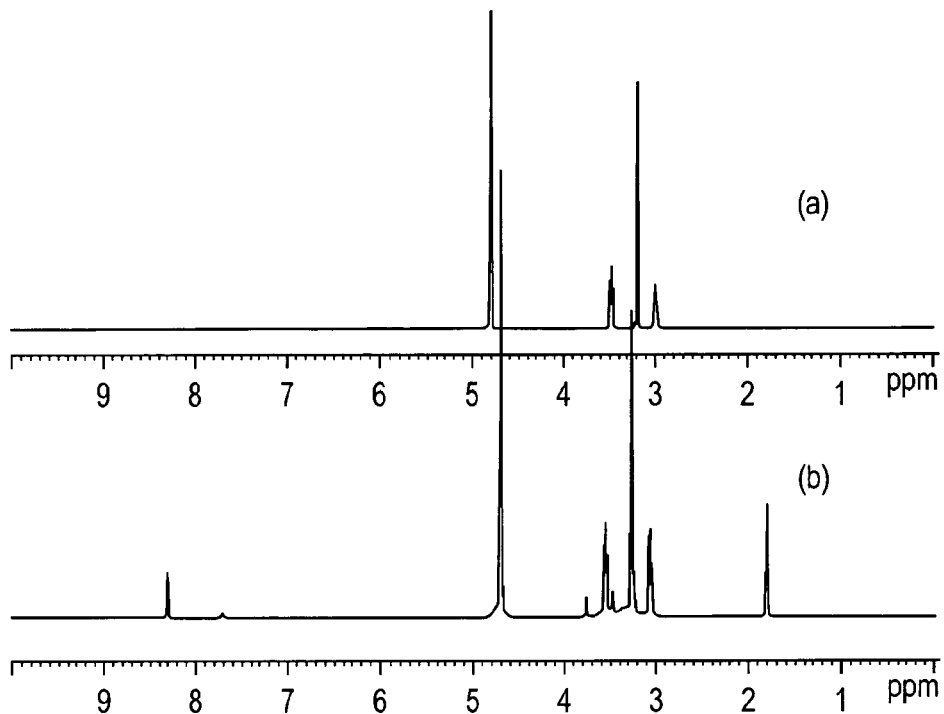
FIGS. 7(a) and (b) show $^1H$ NMR spectra of MEG-TFA in $D_2O$ and YTMS pre-dialysis.
Figure 8:
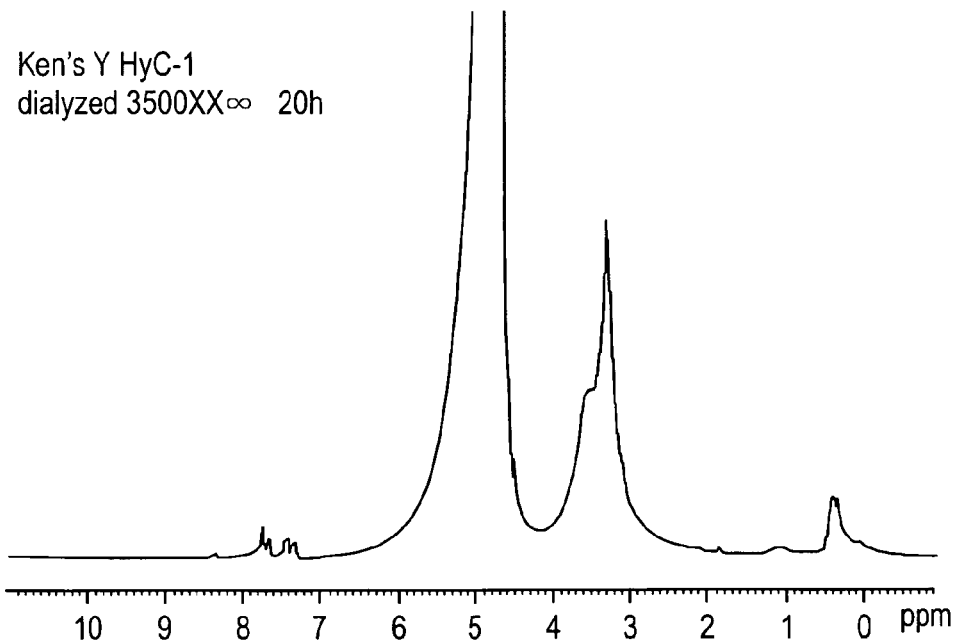
FIG. 8 shows $^1H$ NMR spectrum of post-dialysis Y Hydrochalarone-1 in $D_2O$.

FIGS. 7(a) and (b) are $^1$H NMR spectra of MEG-TFA in $D_2O$ and YTMS-MEG pre-dialysis showing the presence of MEG-H$^+$ with YTMS-MEG in the reaction mixture. FIG. 8 is a $^1$H NMR spectrum of post-dialysis Y Hydrochalarone-1 in $D_2O$ wherein MEG-H$^+$ has been removed by dialysis.

Preparation of Endohedral Metallofullerene Compounds $A_k X_n N@C_m$ metallofullerenes may be prepared by any suitable methods, for example, by using a Krätschmer-Huffman generator. A Krätschmer-Huffman generator typically has a reaction chamber that can be easily evacuated and charged with a controlled pressure of an inert gas such as helium. The generator holds two electrodes within the reaction chamber and is able to apply a potential across the electrodes to produce an arc discharge. WO 2005/097807 provides a detailed description of a process using a Krätschmer-Huffman generator.

In an appropriate method, a mixture of a metal oxide and graphite are filled in a typically cored rod of graphite or other source of carbon. The metal oxide contains the metal to be encapsulated in the fullerene cage. Preferably, the metal oxide may contain the oxide of a rare earth metal or a group IIIB metal in its trivalent form, such as $Er_2O_3$, $Ho_2O_3$, $Y_2O_3$, $La_2O_3$, $Gd_2O_3$, $Tm_2O_3$, $Yb_2O_3$, oxides of other paramagnetic elements and the like. These metal oxides may be used individually or in combination thereof. The mixture of metal oxide and graphite may contain about 20% to about 50% by weight of metal oxide, based on the amount of graphite. Typically, a 47% metal oxide to graphite loading will produce the desired trimetallic nitride endohedral metallofullerene.

When more than one types of metal are to be encapsulated in a fullerene cage, the cored graphite rod can be filled with a mixture of metal oxides and graphite. The relative content of each metal oxide may be from about 20% to 50% by weight. If desired, small amounts of copper may also be added to the mixture to enhance the formation of fullerenes. In one embodiment, copper can be added in an amount of about 9% to about 16% by weight.

The graphite rod filled with the mixture of metal oxide, graphite and optionally copper can then be mounted in a reaction chamber and placed in a Krätschmer-Huffman generator. The gas in the reaction chamber is evacuated and replaced with helium and a small amount of nitrogen gas. Typically, a dynamic atmosphere ranging from about 300 ml/min to about 24250 ml/min helium and about 20 ml/min to about 1000 ml/min nitrogen gas may be utilized. The ratio of helium to nitrogen may vary. The trimetallic nitride endohedral metallofullerenes can be produced for a wide range of helium to nitrogen ratios; however, yields of the metallofullerenes may tend to decrease as the amount of nitrogen approaches the amount of helium. Typically, the ratio of helium to nitrogen may range from about 15 to about 30.

A nitrogen-containing gas is preferred as the source of nitrogen in the trimetallic endohedral metallofullerene. Other nitrogen sources may include, but are not limited to, carbon nitrides. Alternatively or additionally, metal nitrides may be used as sources of both the metal to be encapsulated and nitrogen.

Metallofullerene formation can typically be carried out by causing an arc discharge, for example, by applying a potential across the electrodes. The arc charge consumes the graphite rod and generates a mixture of carbon products which is generally referred to as soot. Within the soot is a wide range of fullerenes including the trimetallic nitride endohedral metallofullerenes. The desired trimetallic nitride endohedral metallofullerenes and other fullerenes can generally be isolated from the resulting mixture by extraction with an appropriate solvent, such as ortho-xylene, carbon disulfide, ortho-dichlorobenzene or toluene.

The extract can preferably be filtered, e.g., through a Nutsche filter, to remove residual insoluble materials, and then purified by a multistage batch chemical process to remove fullerenes, thereby obtaining the desired trimetallic nitride endohedral metallofullerenes at purity levels of 85% or more. For a higher purity, a further chromatographic process can be utilized to provide purity levels over 98%.

Endohedral metallofullerenes represented by formula $A_k X_n@C_m$ can be prepared using similar conditions as described above with the exception that no nitrogen species are added to the reactor.

Reactions of Endohedral Metallofullerenes

The method for covalently attaching substituents to the fullerene cage of an endohedral metallofullerene compound may vary depending on the nature of the substituents.

The present inventors have discovered a new reaction type that provides very favorable route to functionalization of TRIMETASPHERE® molecules. The reaction is based on a unique activated nitrogen-centered radical species generated from a primary amine and a peroxide.

The term "Hydrochalarone," as used herein, refers to the class of compounds resulting from the reaction of the fullerenes, peroxide and amine. Hydrochalarone-1, Hydrochalarone-3 and Hydrochalarone-6 refer to the compounds obtained by using, as the amine, monoethylene glycol (MEG), triethylene glycol, and hexaethylene glycol, respectively.

Although not wishing to be bound by any theory, it is believed that one possible mechanism is that the reaction of a peroxide, such as butanone peroxide, with a primary amine in an organic solvent, such as toluene or xylene, leads to formation of RN(OH)• reactive intermediate that has stability of at least several minutes but not many hours. In the presence of TRIMETASPHERE®, the RN(OH)• reacts rapidly with the benzene rings on the fullerene cage, forming a fullerene radical, which, in turn, may react with other radical or non-radical species present in the reaction mixture. The fullerene radical may also undergo rearrangement internally. In an alternative, the fullerene radical may undergo cleavage of one or more bonds on the fullerene cage.

Figure 9:
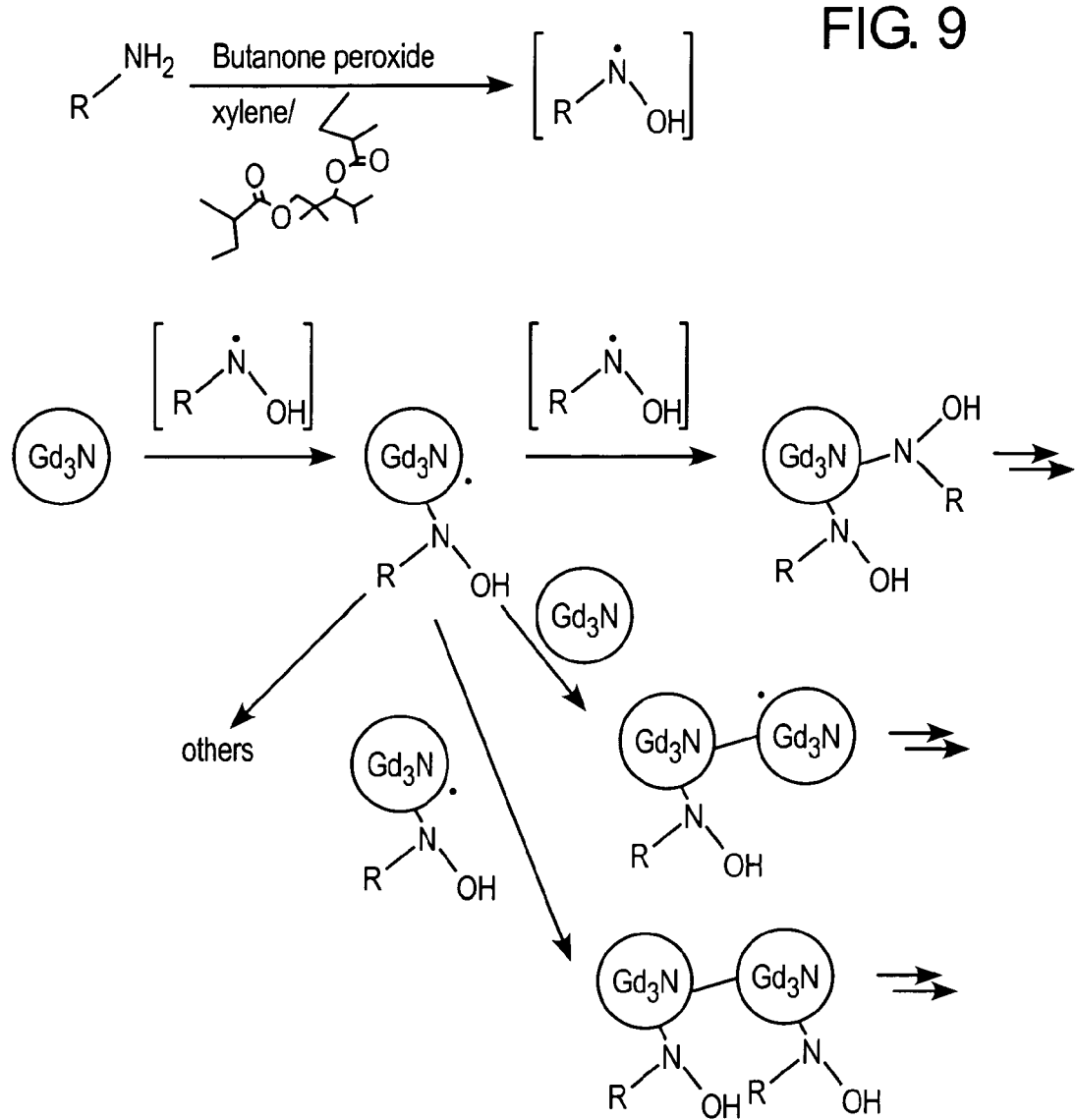
FIG. 9 illustrates a reaction for substitution and polymerization of endohedral metallofullerenes.

The resulting substituted fullerene molecules may be repeatedly reacted with the existing radical species, thereby forming multi-substituted fullerene molecules, polymers or both. Further substitutions may occur at any position of the substituted fullerene, e.g., a carbon atom on the fullerene cage or any site on the branch thereof. FIG. 9 illustrates an exemplary reaction scheme of this process.

Further, FIGS. 10(a) and (b) depict exemplary endohedral metallofullerene dimer and trimer, respectively, in a head-to-head fashion.

Moreover, the RN(OH)• intermediate may undergo rearrangement or other mechanisms to produce an R(NH)O• intermediate, which may react with the benzene rings on the fullerene cage, forming a fullerene radical, in a manner similar to the RN(OH)• intermediate. The resulting fullerene radical may, in turn, undergo the radical reactions described above, form an epoxide, or lead to cleavage of one or more bonds on the fullerene cage.

The substitution reaction is preferably carried out with primary amines. Secondary or tertiary amines generally do not result in the corresponding products. In addition, the peroxide preferably contains butanone peroxide. Other suitable radical initiators, such as t-butyl hydroperoxide and cumene hydroperoxide, can also be used.

Generally, in such a reaction, the amine compound and the peroxide can be used in large excess of the endohedral metallofullerene compound, e.g., in a fullerene:amine:peroxide weight ratio of about 1:15:30. The reaction solvent preferably does not contain ortho-dichlorobenzene.

When a hydrophilic moiety-containing substituent is desired, a primary amine compound containing one or more hydrophilic moiety may be used.

The primary amines used can be quite diverse and include alkyl amines, amino acids, poly ethers, etc. Examples of suitable primary amine compounds may include, but are not limited to, $NH_2(CH_2)_hCH_3$ and $NH_2(CH_2CH_2O)_hCH_3$ wherein h is an integer of 1 or more, and preferably, 1 to 20. Specifically, the primary amine compounds may be represented by the formula $RNH_2$ wherein R is ethyl, propyl, hexyl, dodecyl, $—(CH_2)_4—NH_2$, $—(CH_2)_{10}—NHBoc$, $—(CH_2)_2—COOH$, $—CH(COOCH_2CH_3)(CH_2)_2Ph$, $—CH_2$-18-crown-6, -glyme-OH, -glyme-$OCH_3$, -glyme-NHBoc, -triglyme-OH, -triglyme-$OCH_3$, -triglyme-NHBoc, -hexaglyme-OH, -hexaglyme-$OCH_3$ and -hexaglyme-NHBoc.

Figure 11:
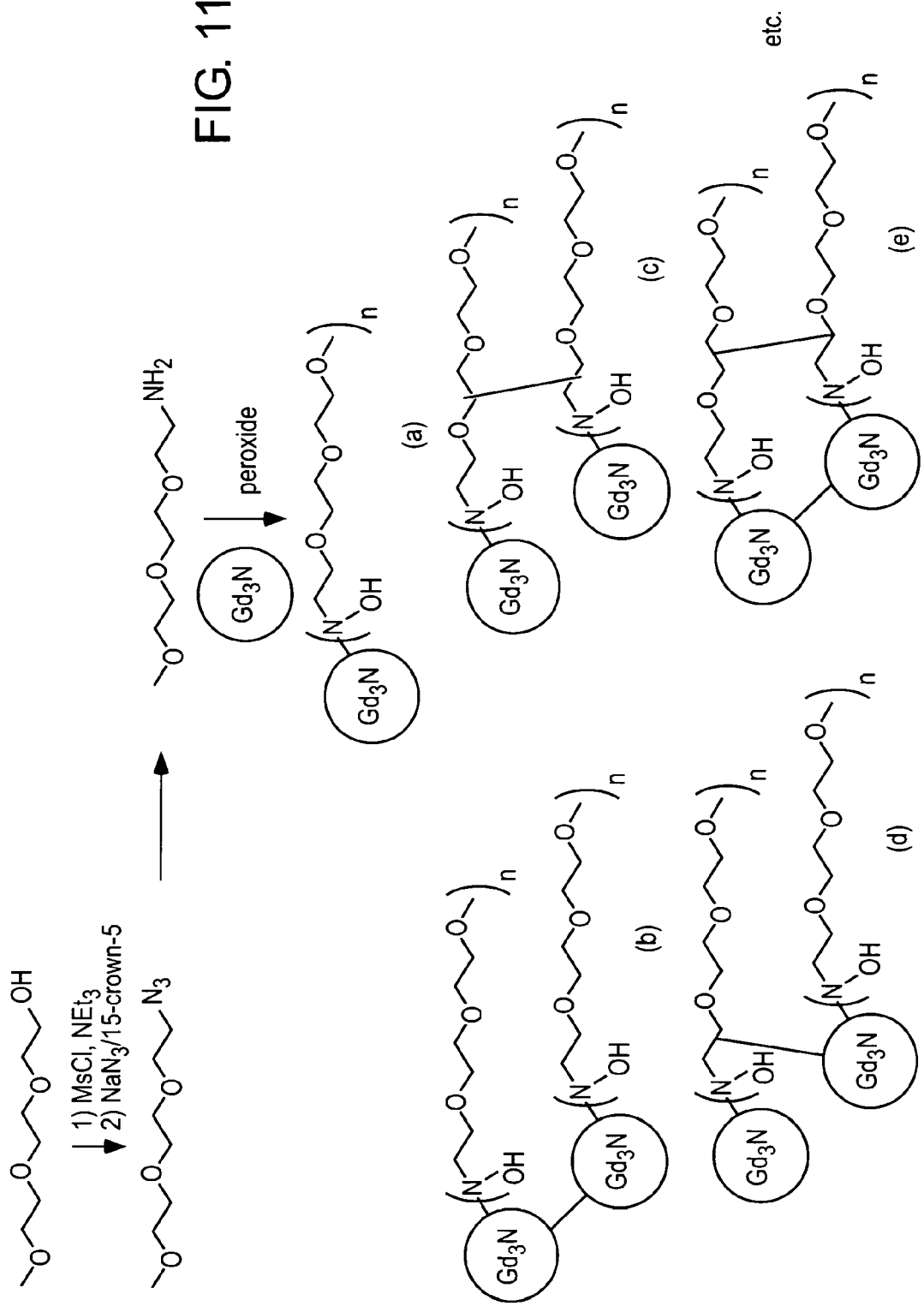
FIG. 11 illustrates one scheme for reaction of $NH_2(CH_2CH_2O)_3CH_3$ with $Gd_3N@C_m$.

FIG. 11 illustrates one specific reaction of $NH_2(CH_2CH_2O)_3CH_3$ with $Gd_3N@C_m$. This specific scheme exemplarily describes formation of multiple substituted fullerene (a) and various dimers in head-to-head fashion (b), tail-to-tail fashion (c), head-to-tail fashion (d) and head-to-head and tail-to-tail fashion (e). It is likely that the reaction mixture may also contain fullerene trimers and other polymers.

It is possible that the resulting substitution reaction products may contain —N(OH)R addition product, —ONHR addition product, —ON=CHR addition product, —NHR addition product or a mixture of two or more of these products.

In a specific example, $^{13}C$ isotopically enriched products obtained in a reaction of $Y_3N@C_{80}$ with $CH_3(CH_2)_5{}^{13}CH_2NH_2$ were studied. After purification by silica chromatography, the products show three peaks in the $^{13}C$ NMR spectrum, at δ 140, 65 and 39 ppm. DEPT NMR further shows that the peak at δ 140 ppm bears one hydrogen atom, while the peaks at δ 65 and 39 ppm bears two hydrogen atoms. Thus, the peak at δ 140 ppm corresponds to a CH=N, which is also consistent with stretch at 1600 $cm^{-1}$ in an IR spectrum. Further, the peak at δ 65 ppm corresponds to a $CH_2$—N(OH), which is also consistent with stretch at 1451-1456 $cm^{-1}$ in an IR spectrum.

Figure 12:
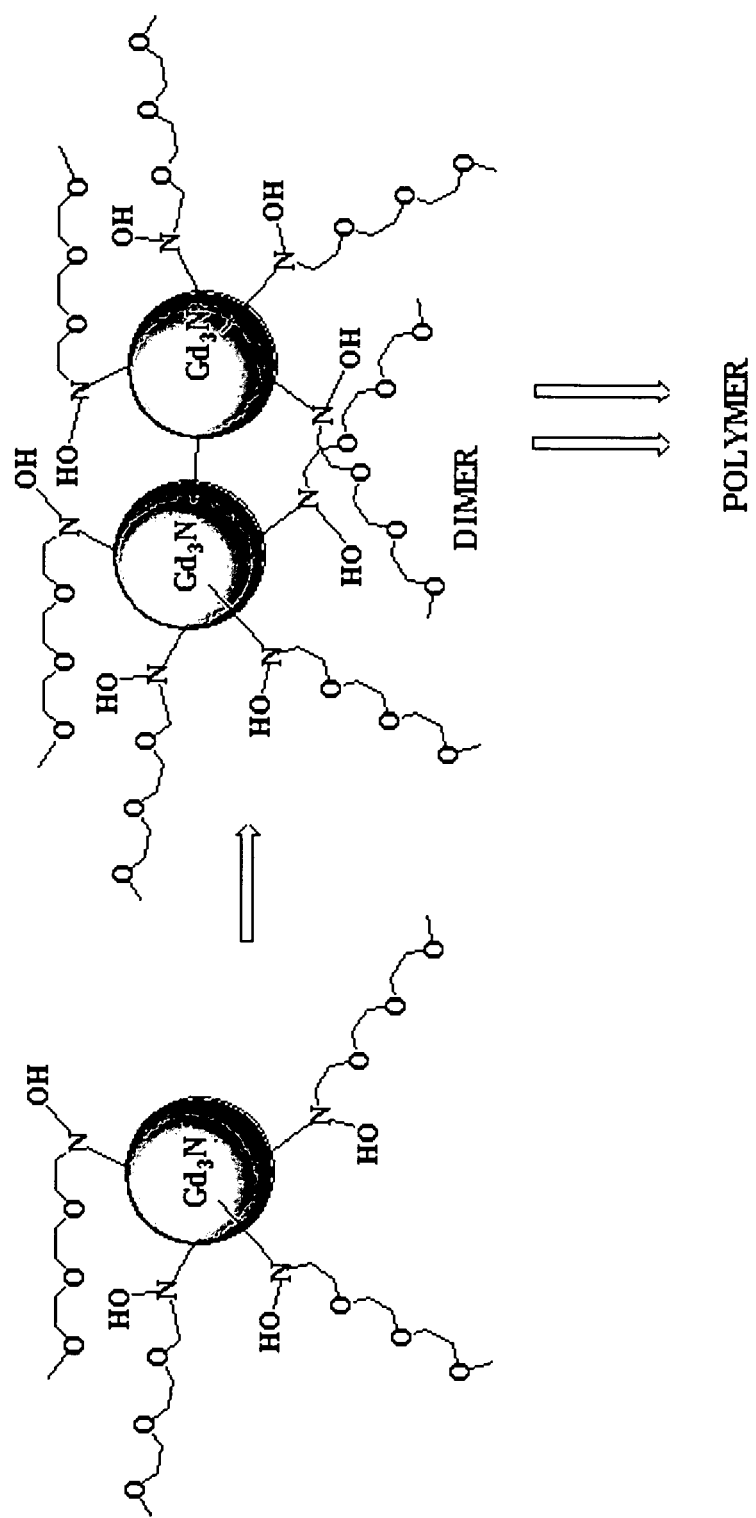
FIG. 12 illustrates an exemplary polymerization reaction scheme of $Gd_3N@C_m[N(OH)(CH_2CH_2O)_3CH_3]_4$.

FIG. 12 illustrates an exemplary polymerization reaction scheme of $Gd_3N@C_m[N(OH)(CH_2CH_2O)_3CH_3]_n$. This scheme depicts the formation of a specific dimer intermediate in head-to-head and tail-to-tail fashion.

A hydroxyl group-containing molecule, such as a sugar, can be treated with an in situ generated metallofullerene radical, radical cation or radical anion, to form C—O bond(s) between the fullerene cage and the hydroxyl-containing molecule.

Additionally, C, O, S and P linkages can also be achieved using radical chemistry. Namely, pre-generated C, O, S and P radicals can readily react with metallofullerenes to form C—C, C—O, C—S and C—P bonds, respectively. Carbon radicals may be free radicals or radical equivalents, such as, but not limited to, generated from reaction of Grignard reagents and Cu(I)Br.

Carbon linkages may also be made using established fullerene chemistry, such as, but not limited to, cyclopropanation ("Bingel reaction"), diazo addition, pyrrolidine addition ("Prato reaction"), nucleophilic carbon reactions (such as addition of carbon lithium salts), [4+2] cycloadditions (such as "Diels-Alder reactions"), [3+2] cycloadditions, and carbene additions.

As described herein, in a reaction mixture, the type and/or number of substituents and holes, on each endohedral metallofullerene cage may vary, depending, to some extent, on the nature of substituents and reaction conditions. Thus, it is likely that any particular reaction may generate a mixture of endohedral metallofullerene compounds having different type and/or numbers of substituents and/or holes on the fullerene cages.

For instance, in reactions of $Gd_3N@C_{80}$ with methyl ether oligoethylene glycol amines, i.e., $CH_3(OCH_2CH_2)_nCH_3$, n is 1, 3, 6 and 11, in xylene, the number of resulting $Gd_3N@C_{80}$ addends decreases with increasing chain length, from 6-12 for n=1 to 3-6 for n=6. This dependency may show that the reaction is self-limiting. The products are not soluble in xylene and precipitate when they became sufficiently polar, thereby causing the reaction to stop.

When a metallofullerene compound having more than one types of substituents is desired, the substitution sequence may vary and can be optimized by those skilled in the art. For example, when preparing a compound represented by the formula (II), i.e., $A_tX_nN_t@C_m^{}$, wherein the substituents in $C_m^{}$ contain both Z' and Q', Z' may be introduced first to the corresponding endohedral metallofullerene followed by Q', or vice versa.

The present invention is further illustrated by the following specific examples but is not limited hereto.

EXAMPLES

Unless specified, all the commercially available materials were used herein without further purification. All the measurements including weight and temperature were uncorrected.

Measurement—Relaxivity

Relaxivity was measured using a Maran Ultra bench-top relaxometer (Oxford Instruments, UK) with a permanent magnetic field at about 0.55 T, corresponding to proton magnetic frequency of about 23 MHz. The measurement temperature was kept constant at 40° C.

Measurement—Average Hydrodynamic Radius

The hydrodynamics radius was measured using Dynamic Light Scattering with a commercial instrument (Zetasizer Nano-S90 from Malvern Instruments).

Example 1

Preparation of Endohedral Gadofullerene Compound Using $NH_2(CH_2CH_2O)_3CH_3$ $Gd_3N@C_{80}$ (10 mg) was taken in xylene (4.0 mL). $NH_2(CH_2CH_2O)_3CH_3$ (250 mg) and butanone peroxide (1500 mg of a 31% commercially available solution in 2,2,4-trimethyl-1,3-pentanediol diisobutyrate) were added. The mixture was sonicated (30 s), then shaken at 75° C. for 60 minutes. During this time a precipitate formed. The reaction mixture was cooled and the xylene was decanted. The remaining oily precipitate was washed with toluene (5 mL×2) and diethyl ether (5 mL×2). The product was then dissolved in DI water (10 mL), and baked in a 50° C. oven for 7 days. It was then dialyzed with 1000 MWCO tubing against 10 mM Trizma acetate (pH=7.2) for 3 days (3 buffer changes of 3 l each). The relaxivity ($r_1$) of this material was measured to be 90 mM$^{-1}$S$^{-1}$. The particle size was determined using DLS to be less than 10 nm. The relaxivity of the resulting solution was measured by obtaining a T1 measurement, then ashing a sample at 900° C. The white ash was dissolved in concentrated HCl over 4 hours. The T1 of the resulting solution was measured and compared to a standard concentration curve, thereby determining the concentration of the Gd.

Further, there were no aggregates observed by dynamic light scattering.

Figure 13:
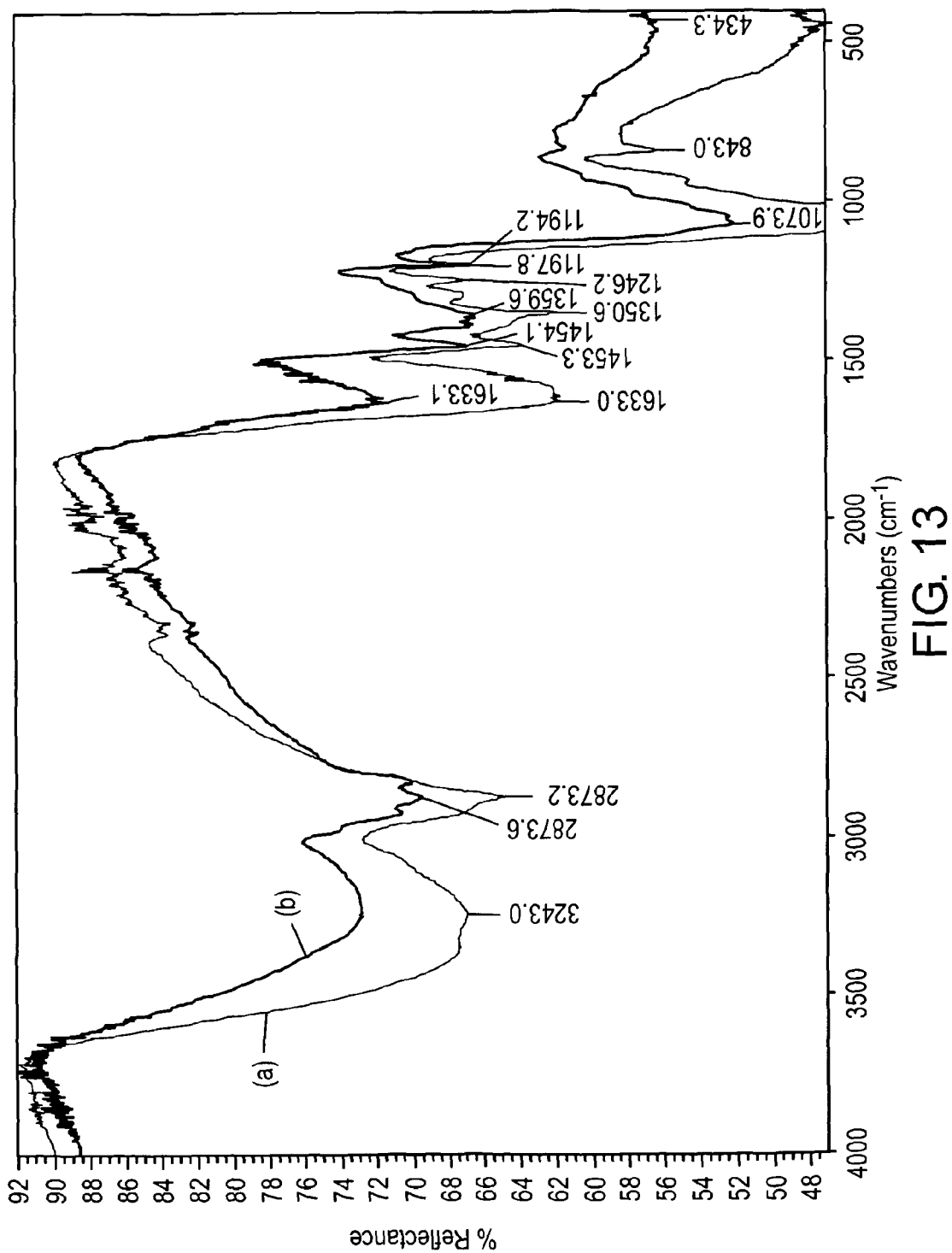
FIGS. 13(a) and (b) show IR spectra of $C_{70}$-MEG and Hydrochalarone-3.

FIGS. 13(a) and 13(b) are IR spectra of $C_{70}$-MEG and Hydrochalarone-3 (low peroxide preparation), which show the peak at about 1452 cm$^{-1}$ associated with hydroxylamines.

Elemental analysis for Hydrochalarone-3 indicates a product with 12 pendent groups having the formula $C_{164}H_{192}O_{48}N_{13}Gd_3$ (FIG. 14). It is noted that in elemental analysis of TRIMETASPHERE®s, incomplete combustion of the cage is a persistent problem. For example, samples of pure, unfunctionalized materials, such as $Sc_3N@C_{80}$, routinely result in low carbon analysis. This is undoubtedly due to the high stability of these materials, as reflected in the TGA.

Example 2

Preparation of Endohedral Gadofullerene Compound Using $NH_2CH_2CH_2OCH_3$

To a solution of $Gd_3N@C_{80}$ (Gd TMS) (2.8 mg) in xylene (7 mL) was added methoxyethylamine (52 mg) and butanone peroxide (110 mg of a 31% solution in 2,2,4-trimethyl-1,3-pentanediol diisobutyrate). The reaction mixture was agitated for 16 hours and then extracted with water twice (5 mL and 2 mL, respectively). The water extracts were then dialyzed through 1000 MWCO tubing against Trizma acetate (10 mM). The combined aqueous extracts exhibited a relaxivity of about 90 mM$^{-1}$·S$^{-1}$.

Figure 15:
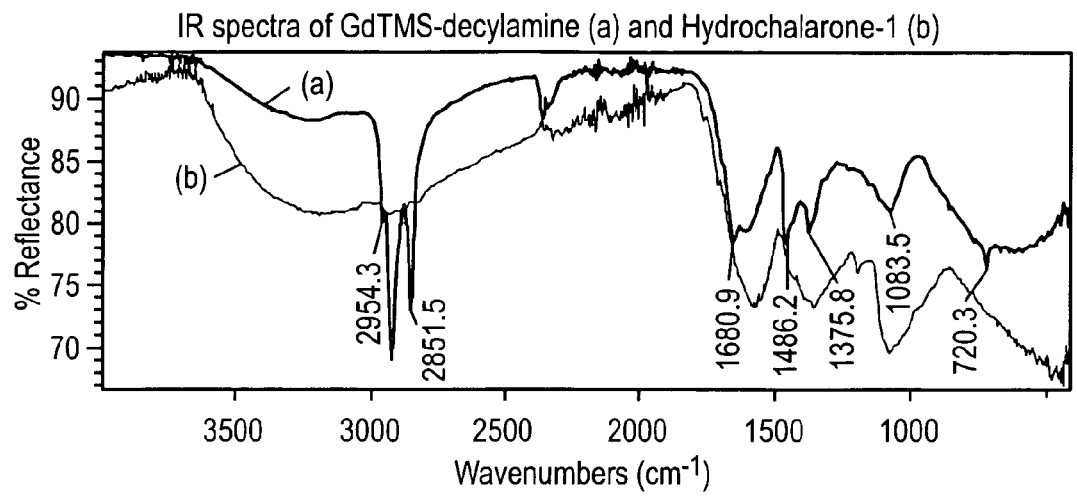
FIGS. 15(a) and (b) show IR spectra of GdTMS-decylamine and Hydrochalarone-1.

FIGS. 15(a) and 15(b) are IR spectra of GdTMS-decylamine and

Hydrochalarone-1 showing C—O stretch (at about 1100 cm$^{-1}$) in a non-ether amine product. It is noted that GdTMS-decylamine is ether soluble while Hydrochalarone-1 is water soluble.

Figure 16:
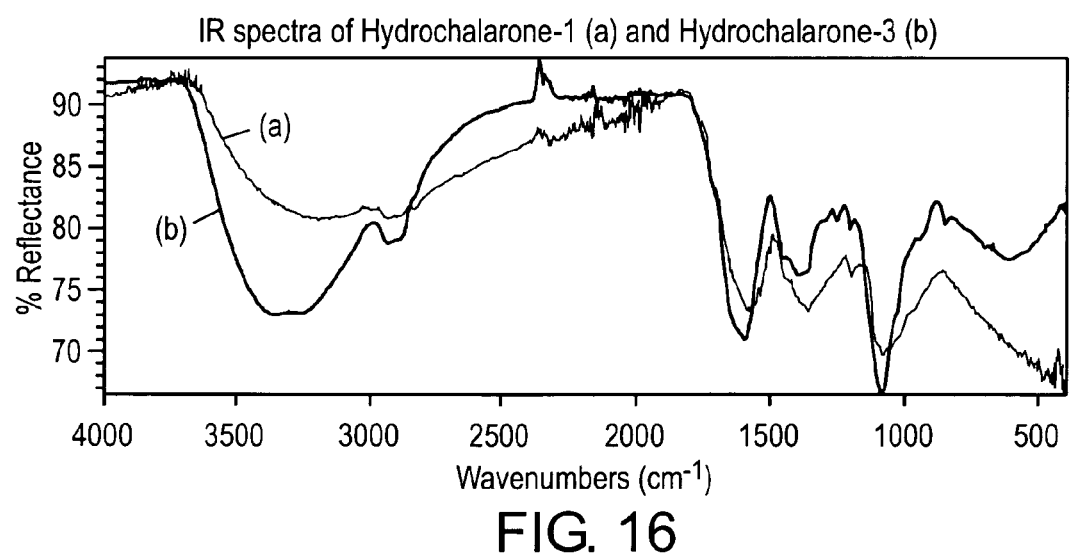
FIGS. 16(a) and (b) show IR spectra of Hydrochalarone-1 and Hydrochalarone-3.

FIGS. 16(a) and 16(b) are IR spectra of Hydrochalarone-1 and Hydrochalarone-3.

Example 3

Preparation of Endohedral Gadofullerene Compound Using $NH_2(CH_2CH_2O)_6CH_3$

In the same manner described in Example 2, $Gd_3N@C_{80}$ (4 mg) and $NH_2(CH_2CH_2O)_6CH_3$ (60 mg) were dissolved in xylene (12 mL) with sonication. To the resulting solution was added butanone peroxide (120 mg of a 31% solution in 2,2,4-trimethyl-1,3-pentanediol diisobutyrate). The reaction mixture was agitated for 16 hours at room temperature, during which precipitate formed. The resulting mixture was then extracted with water three times (3-4 mL each time). The combined aqueous extracts were dialyzed with 1000 MWCO tubing. The resulting solution exhibited a relaxivity of 180 mM$^{-1}$·S$^{-1}$, as determined by the ashing method described above.

Figure 17:
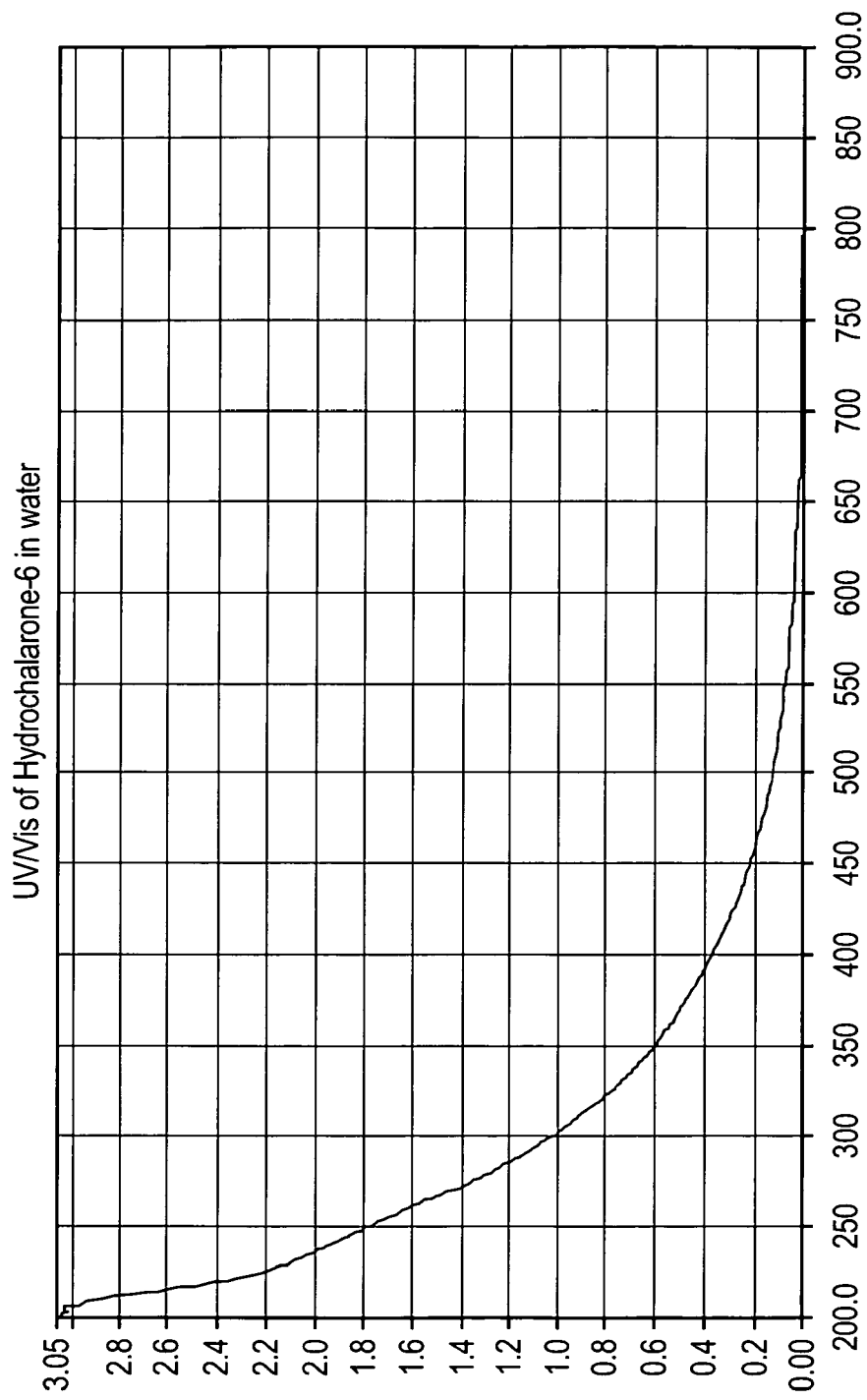
FIG. 17 shows UV/Vis spectrum of Hydrochalarone-6 in water.

FIG. 17 is UV/Vis of Hydrochalarone-6 in water.

Figure 18:
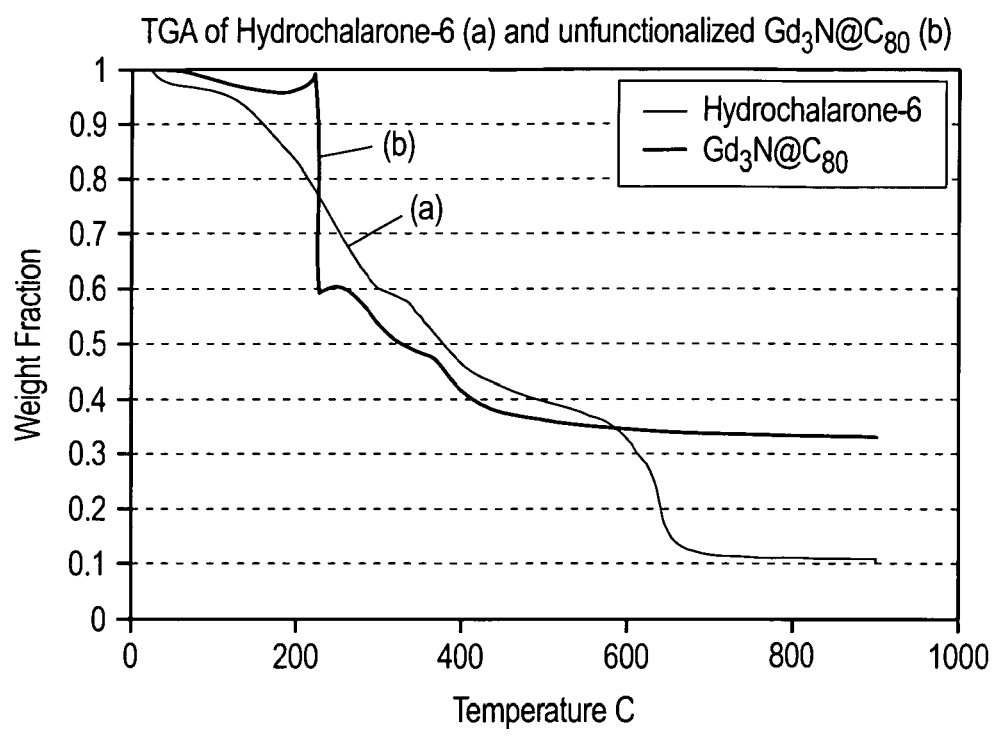
FIGS. 18(a) and (b) show TGA spectra of Hydrochalarone-6 and unfunctionalized $Gd_3N@C_{80}$.

FIGS. 18(a) and (b) are TGA of Hydrochalarone-6 and unfunctionalized $Gd_3N@C_{80}$, which show weight loss vs. temperature. FIG. 18(b) shows that the unfunctionalized TMS starts to decompose around 200° C. and is completely decomposed at 400° C., while the Hydrochalarone derivative cage doesn't decompose until around 600° C. The rapid weight loss at around 600° C. is believed to due to the decomposition of the fullerene cage, based on the mass before the weight loss relative to the final mass, which is $Gd_2O_3$.

Example 4

Preparation of GdTMS-Glucosamine

Tetra-O-acetyl-glucosamine (60 mg), $Gd_3N@C_{80}$ (2.5 mg) and butanone peroxide (115 mg of a commercially available 31% solution in 2,2,4-trimethyl-1,3-pentanediol diisobutyrate) were combined in xylene (7 mL). The resulting solution was agitated for 16 hours. After removal of xylene in vacuo, the remainder was dissolved in a MeOH:H$_2$O (10 ml:15 mL) mixture. To the resulting mixture was added a saturated NaOH solution (2 mL). This solution was sat for 2 days at room temperature, condensed to 1 mL to remove methanol, and diluted to 5 mL with water After filtration through a 0.2 micron syringe filter, the solution was dialyzed with 1000 MWCO tubing and the relaxivity was measured ($R_1$=5 mM$^{-1}$·S$^{-1}$ (assuming a 100% conversion of starting material and a 100% extraction). After heating to 60° C. for about 20 minutes, the $R_1$ rose to 8 mM$^{-1}$·S$^{-1}$.

Example 5

Control Experiments

Reaction of an amino ether and a peroxide yielded a colorless product with no measurable relaxivity. In addition, reaction of an amino ether, a peroxide and $C_{60}$ yielded a yellow fullerene product that has a negligible relaxivity.

Example 6

Preparation of GdTMS[PMCD]

$Gd_3N@C_{80}$ (5.0 mg) was suspended in anhydrous DMF (5.0 mL) under an inert nitrogen atmosphere. The resulting suspension was vigorously stirred and subsequently treated with a large excess of potassium superoxide powder (8.0 mg). Subsequently, to the above suspension, 10.0 mg of 8-crown-6 was added. As the reaction proceeded, GdTMS gradually dissolved to form a dark solution. The reaction mixture was stirred for additional 30 minutes and then PMCD (permethylated beta-cyclodextrin, 10 equiv.) was added. After 1-2 hours of vigorous stirring, the solvents were removed under vacuum. The residue was dissolved in de-ionized water (5.0 mL). The resulting colored aqueous solution was filtered via a 0.45 micrometer syringe filter before being subjected to SEPHADEX G-25 flash column purification and/or dialysis.

The GdTMS[PMCD] product showed a relaxivity of about 35 to 40 mM$^{-1}$·S$^{-1}$ in DI water and a typical particle size in serum of about 20 nm to about 90 nm.

While various embodiments have been described with reference to specific embodiments, variations and modifications may be made without departing from the spirit and the scope of the invention. Such variations and modifications are to be considered within the purview and scope of the invention as defined by the appended claims.

All of the above-mentioned references are herein incorporated by reference in their entirety to the same extent as if each individual reference was specifically and individually indicated to be incorporated herein by reference in its entirety.

What is claimed is:

1. An endohedral metallofullerene compound represented by the formula (III): $A_kX_nN_i@C_m'$,
   wherein A and X represent identical or different elements in the periodic table of elements, provided that at least one of A and X is paramagnetic;
   $C_m'$ represents a fullerene having one or more missing carbon atoms and/or bonds, wherein the fullerene is derived from $C_m$, which may optionally be substituted;
   $C_m$ represents a fullerene molecule having m carbon atoms;
   k represents an integer from 1 to 3;
   n represents an integer from 0 to 2, provided that $1 \leq k+n \leq 3$;
   i represents an integer of 0 or 1; and
   m represents an even integer from about 60 to about 200.

2. The compound of claim 1, which in water has a relaxivity of about 30 $mM^{-1} \cdot S^{-1}$ to about 300 $mM^{-1} \cdot S^{-1}$ and forms a dispersion in water with entities having an average hydrodynamic radius of less than 20 nm.

3. The endohedral metallofullerene compound of claim 1, wherein at least one of A and X represents a rare earth element or a group IIIB element in the periodic table of elements.

4. The endohedral metallofullerene compound of claim 1, wherein at least one of A and X is selected from the group consisting of scandium, yttrium, lanthanum, gadolimium, holmium, erbium, thulium, dysprosium, terbium and ytterbium.

5. The endohedral metallofullerene compound of claim 1, wherein $A_kX_nN_i@C_m'$ represents $Gd@C_{60}'$, $Gd@C_{82}'$ or $Gd_3N@C_{80}'$.

6. The endohedral metallofullerene compound of claim 1, wherein the substituent(s) in $C_m'$ further comprise one or more targeting species selected from the group consisting of cholesterol, L-DOPA, tropane or its derivatives, tetrabenazine, urushiol, transferrin, muc-1, antibodies, cytokines, saccharides, polysaccharides, glutamate and aminolevulinic acid.

7. The endohedral metallofullerene compound of claim 1, wherein the $C_m'$ is optionally substituted by:
   (a) one or more groups which are directly bonded to $C_m$ via an atom selected from the group consisting of N, O, S and P, and/or
   (b) one or more groups comprising a hydrophilic moiety.

8. The endohedral metallofullerene compound of claim 1, wherein $C_m'$ is substituted with at least one selected from the group consisting of an oxygen atom and a —COOH group.

9. A composition comprising the endohedral metallofullerene compound of claim 1.

* * * * *